United States Patent
Hamas

[19]

[11] Patent Number: 6,053,927
[45] Date of Patent: Apr. 25, 2000

[54] APPARATUS AND METHOD FOR IMPLANT REMOVAL

[75] Inventor: Robert S. Hamas, Dallas, Tex.

[73] Assignee: RSH-GS Trust, Dallas, Tex.

[21] Appl. No.: 09/173,234

[22] Filed: Oct. 15, 1998

[51] Int. Cl.[7] .................................................. A61B 17/10
[52] U.S. Cl. .......................... 606/138; 606/167; 606/172
[58] Field of Search .................................. 606/138, 167, 606/172, 181

[56] References Cited

U.S. PATENT DOCUMENTS

| | | | |
|---|---|---|---|
| 1,045,906 | 12/1912 | Sweet | 606/167 |
| 5,545,173 | 8/1996 | Herbst | 606/181 |
| 5,823,970 | 10/1998 | Terwilliger | 600/564 |

*Primary Examiner*—Michael Buiz
*Assistant Examiner*—Lien Ngo
*Attorney, Agent, or Firm*—Jenkens & Gilchrist

[57] ABSTRACT

A surgical device for removing implanted devices includes a sleeve device with an elongated trough portion arranged to extend through a skin opening and be positioned subjacent to a particular implanted device. A removable knife assembly is inserted through a tubular portion of the sleeve device and is used to incise scar tissue from a proximal end of the implanted device. The implanted device is then manipulated through the opening in the surrounding scar tissue and deposited on the trough portion of the sleeve device whereupon it is removed through the skin opening. The surgical device may also include a removable trochar device slidably engaging the tubular portion of the sleeve device and penetrating flesh to the implanted device.

23 Claims, 4 Drawing Sheets

FIG. 6 ic device for removing implanted devices has a sleeve device and a
APPARATUS AND METHOD FOR IMPLANT REMOVAL

BACKGROUND OF THE PRESENT INVENTION

1. Field of the Invention

The present invention is directed to an apparatus and associated method for the removal of surgically implanted devices from within a living body.

BACKGROUND AND OBJECTS OF THE PRESENT INVENTION

With ever increasing advances in medicine and the improvements in living conditions worldwide, a so-called population explosion has occurred where the number of humans on the earth rises geometrically. At present, there are about six billion human beings and this number is expected to more than double within a few decades. As with any unchecked organism, there is an obvious need to curb or even halt the growth rate of a population. With humans, chemical contraceptives and mechanical birth-control devices, e.g., condoms, are presently utilized in an effort to prevent conception and pregnancy. Should conception occur, however, the developing zygote and fetus may be terminated or aborted through other birth-control techniques at present controversial in some countries and forbidden in others.

Since contraception is preferred over abortion in most societies, significant advances have been made in analyzing human physiology, particularly, the human female hormonal cycles, to address this issue. Contraceptive pills ("The Pill") and capsules have now been employed for decades with significant success. Obvious problems associated with such oral contraceptives is the need for the woman to monitor their hormonal cycle and ingest the required dosage to effectuate contraception. Failure to adhere to the prescribed regimen could result in conception and pregnancy. Such vigilance, however, requires a measure of maturity and responsibility, qualities frequently lacking in young sexually active girls as well as women in the Second or Third World who lack the education and understanding needed to properly administer the drugs. Further, access to contraceptives may be strictly controlled. In addition to the problems of dosage regularity and easy access, there is the issue of cost. Although contraceptives are relatively inexpensive in Western societies, for many countries, such as China and in Africa, a daily dosage of contraceptives is economically impractical or impossible.

There has thus developed the need to produce a more effective, longer term contraceptive that could administer the requisite dosage to prevent conception without the requirement of complicated procedures and cost.

One such approach is levonorgestrel implants, such as the NORPLANT® SYSTEM, an implantable device which at present utilizes a set of six flexible closed tubes, called capsules, made of Silastic® (dimethylsiloxane/methylvinylsiloxane copolymer). Each capsule contains 36 mg of progestin levonorgestrel, a contraceptive, and is about 2.4 mm in diameter and 34 mm in length. As will be discussed further hereinafter, the capsules are implanted in a superficial plane beneath the skin of the upper arm. Diffusion of the levonorgestrel through the capsule walls provides a continuous low dose of the progestin over a period of about 5 years. In particular, the levonorgestrel inhibits ovulation and the thickening of the cervical mucus, a precursor for egg implantation. The NORPLANT® SYSTEM is, therefore, indicated for the prevention of pregnancy and is a long-term (e.g., up to about 5 years) reversible contraceptive system. At the end of the 5th year, the spent capsules should be removed, and new capsules inserted at that time should continuing contraceptive protection be desired.

In addition to contraceptives, other implant devices may be used for drug delivery and for other purposes. As with the NORPLANT® SYSTEM discussed hereinabove, any implanted device, being a foreign body, may require subsequent removal and replacement.

Since the implanted devices remain in the body for long intervals, however, removal can be problematic and requires a measure of skill to perform properly and minimize trauma and physical disfigurement. As a result of surrounding scar tissue formation and/or improper insertion of the implanted devices, a routine removal procedure can become quite complicated and additional incisions may be required to remove the implanted devices, further increasing trauma and potentially disfiguring external marks.

There is, accordingly, a need for improvements in the tools and methods utilized in the removal of long-term, implanted devices, such as those employed in the NORPLANT® SYSTEM.

A first object of the present invention, therefore, is to provide an improved tool for the removal of implanted devices that minimizes trauma and the number of incisions.

A second object of the present invention is to provide an improved method and technique whereby implanted devices are removed from the body.

SUMMARY OF THE INVENTION

In one aspect of the present invention, the surgical device for removing implanted devices has a sleeve device and a removable knife assembly. The sleeve device has a handle portion, a tubular portion aligned in predetermined relationship with the handle portion, and an elongated trough portion having a predetermined length extending outwardly from the sleeve portion and aligned therewith. The elongated trough portion also has a tip disposed at a distal end thereof. The removable knife assembly is adapted to be selectively insertable through the tubular portion of the sleeve device. The knife assembly has a generally cylindrical, elongated support section, a handle portion at a proximal end of the support section, and a blade disposed at a distal end of the support section. The spatial orientation of the handle portion cain control and hold the spatial orientation of the knife blade. The support section has a length sufficient to position the blade of the knife assembly at selected locations of the elongated trough section of the sleeve device when the moveable knife assembly is inserted through the tubular portion of the sleeve device. Other features of the surgical device for removing implanted devices, in accordance with the present invention, include the tip disposed at the distal end of the trough portion having a sharp point adapted to penetrate subcutaneous flesh tissue. In a second aspect of the present invention, the device has a removable trochar device. The removable trochar device has a handle portion adapted to abut the handle portion of the sleeve device, and a generally cylindrical member extending outwardly from the handle portion of the trochar device and adapted to be slidably received in the tubular and trough portions of the sleeve device. The generally cylindrical member has a length sufficient to extend a distal end of the cylindrical member beyond the tip of the elongated trough portion of the sleeve device when the removable trochar device is inserted through the tubular portion of the sleeve device. The distal end of the trochar device has a sharp tip, or point, adapted to puncture subcutaneous flesh tissue when the sharp point is extended beyond the distal end of the trough portion of the sleeve device. The trocar device also may have an arcuate trough portion disposed adjacent the distal end of the cylindrical member to help in trapping the implanted device within the trough portion, facilitating manipulation.

Other features of the surgical device embodying the present invention include the blade, disposed at the distal end of the support section of the removable knife assembly, having a distal tip and a guard member spaced a predetermined distance from the distal tip, whereby the penetration of the blade into surrounding scar tissue and/or implanted device is limited to the predetermined distance.

In another aspect of the present invention, a method for surgically removing an implanted device from a patient includes palpating the surface of the patient's skin in an area above the implanted device and determining the position and orientation of the implanted device. An axis aligned with the implant is then defined and an incision made through the skin along the defined axis at a position proximate an end of the implanted device. The incision is preferably the one used to previously insert the implanted device. A surgical device having a sleeve device with an elongated trough portion is then aligned with the incision in the skin and the implant, and the sleeve device inserted through the incision. The sleeve device is then advanced so that at least some of the trough portion is positioned below the implant. The trough portion of the sleeve device is then lifted toward the skin, thereby trapping the implant between the trough portion of the sleeve device and the skin. The surgical device further includes a removable knife assembly which is then inserted through the tubular portion of the sleeve device and advanced through the tubular portion and along the trough portion until a blade disposed at a distal end of the knife assembly is positioned at a distal end of the elongated trough portion of the sleeve device. The knife assembly is then rotated so that the blade is directed toward the implant and then again advanced, whereby scar surrounding the implant is incised sufficiently to permit the implant to pass through the incised scar tissue. The removable knife assembly is then withdrawn from the sleeve device and fingertip pressure applied to the skin surface above the implant and the implant manually urged into and along the trough portion of the sleeve device. When the implant is visible through the skin incision, it is removed from the trough portion of the sleeve device.

Other features of the method for surgically removing an implanted device in accordance with the present invention include the surgical device having a removable trochar device that is adapted to be slidably received in the tubular and trough portions of the sleeve device. When inserting the surgical device (consisting of combined trochar and sleeve devices) through the incision and advancing a distal end of the elongated trough portion of the combined trochar and sleeve devices, the method includes advancing a distal end of the combined trochar and sleeve devices so that at least some of the trough portion of the trochar device is subjacently positioned under the implanted device between the implanted device and the trough portion of the trochar device. When the surgical device includes the removable trochar device, the removable trochar device is withdrawn from the tubular and trough portions of the sleeve device prior to inserting the removable knife assembly through the tubular portion of the sleeve device.

Additional features of the method for surgically removing a subdermal or other subcutaneous implanted device in accordance with the present invention include the incising of an opening through the skin at a position previously incised for insertion of the implanted device.

Yet other features of the method include marking the skin over the implanted device after palpating the surface of the patient's skin above the proximate position of the implanted device.

Still other features of the method for surgically removing implanted devices in accordance with the present invention include sequentially surgically removing a plurality of implanted devices through the same skin incision.

A more complete appreciation of the present invention and the scope thereof can be obtained from the accompanying drawings which are briefly summarized below, the following detailed description of the presently-preferred embodiments of the invention, and the appended claims.

BRIEF DESCRIPTION OF THE DRAWINGS

A more complete understanding of the method and apparatus of the present invention may be obtained by reference to the following Detailed Description when taken in conjunction with the accompanying Drawings wherein:

FIGS. 3A and 5B are side and end-on views, respectively, of a knife assembly employed in conjunction with the sleeve device component of the implant removal device of the present invention, as shown in FIG. 1.

DETAILED DESCRIPTION OF THE PRESENTLY PREFERRED EXEMPLARY EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

In conventional techniques for implanted device removal, particularly NORPLANT®, the implanted tubes or capsules are located by palpating the area in question (the upper arm) and possibly marking their position with a skin marker. A small amount of local anesthetic is then injected under the capsule ends nearest the original insertion incision site, which serves to raise the ends of the capsules. An incision is then made near the ends of the capsules. Since the capsules have usually been implanted for some time, a scar tissue sheath normally forms around each capsule. The individual capsules may be digitally pushed towards the incision with the fingers until the tip of the scar-tissue-sheathed capsule is visible. However, mere digital manipulation usually does not suffice because the surrounding scar tissue sheath restricts mobility of the capsule. In most situations, a surgical grasping instrument such as a hemostat must be inserted into the incision, probed under the skin to find and grasp the scar-tissue-sheathed capsule, and then pulled to draw the scar-tissue-sheathed capsule into the incision so that it is visible. Removal of the capsule typically requires cutting through the visible scar tissue sheath with a scalpel blade to expose the capsule tip which can then be grasped and pulled out of the scar tissue sheath with forceps.

As noted, a chief problem in NORPLANT® or other long-term implant removal is visualizing the scar tissue sheath of the capsule so it can be incised to expose the capsule within. This may require additional skin incisions and/or the trauma of repeated probing and grasping under the skin with a surgical instrument to find and pull the scar-tissue-sheathed implant into the incision so it is visible and the scar-tissue-sheath can be incised. As set forth herein, the present invention is directed towards improvements in the technique of capsule removal that minimizes the traumatic and other deleterious effects encountered in conventional techniques.

Figure 1:
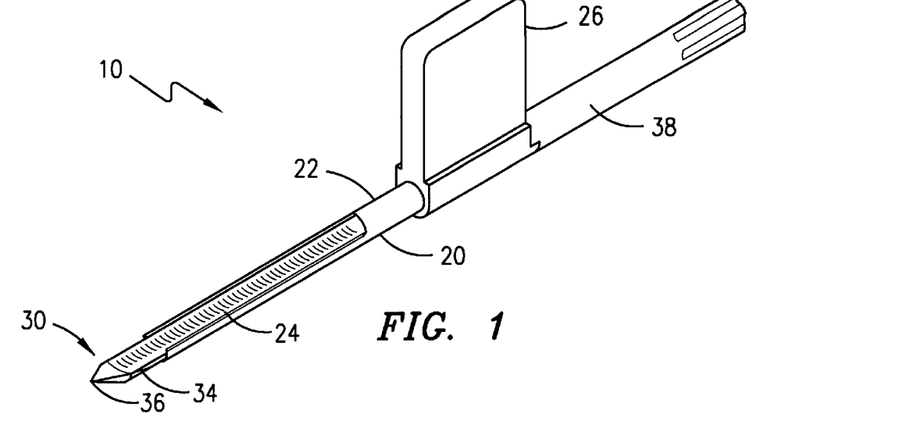
FIG. 1 is a perspective view of an embodiment of a portion of the implant removal device as set forth in the present invention, illustrating a combination of a sleeve device and a trochar device.

With reference now to FIG. 1 of the drawings, there is illustrated perspective view of a first embodiment of the apparatus of the present invention. As shown in the figures, the surgical implant removal device, a portion of which is generally designated by the reference numeral 10, includes a combined sleeve device 20 and a removable trochar device 30, each respectively illustrated in more detail in FIGS. 2A, 2B, 3A, and 3B, and a removable knife assembly 50, illustrated in more detail in FIG. 5, which combines with the sleeve device 20, as described in more detail hereinafter.

Figure 2A:
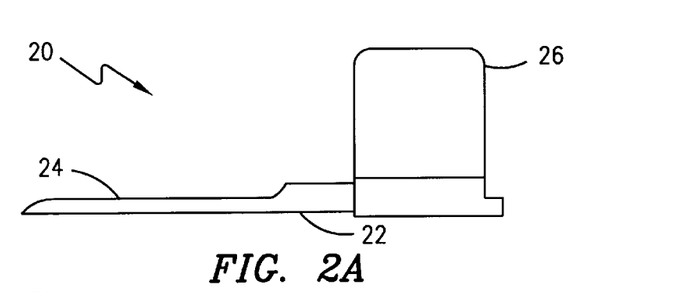
FIGS. 2A and 2B are side and end-on views, respectively, of the sleeve device component of the implant removal device of the present invention, as shown in FIG. 1.
Figure 2B:
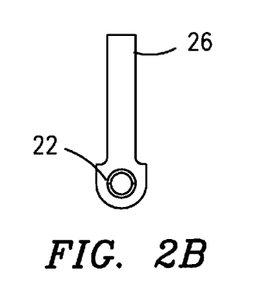

With reference now to FIG. 2A, the sleeve device 20 has a generally cylindrical tube or cannula 22 portion. A trough portion 24 extends outwardly from the tubular portion 22 and has a hemicylindrical shape (less than 50% encirclement, e.g., about 40%) and a distal end spaced from the tubular portion 22. A thumb grip handle portion 26, at the other end of the sleeve device 20, is used to manipulate the sleeve device 20 through an incision to a given implant, as described and illustrated in more (detail hereinafter. In other words, the handle portion 26 is aligned with the opening in the sheath, i.e., the trough portion 24, so that when the handle is upright, the opening is facing up, providing the user with a ready spatial cue as to the orientation of the sleeve device 20 within the patient. FIG. 2B illustrates an end-on view of the sleeve device 20 shown in FIG. 2A.

Figures 3A, 3B:
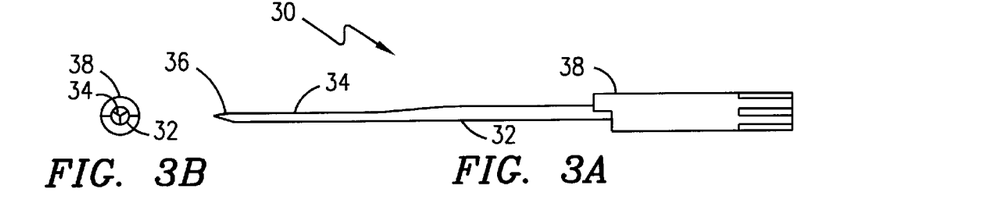
FIGS. 3A and 3B are side and end-on views, respectively, of the trochar device component of the implant removal device of the present invention, as shown in FIG. 1.

The removable trochar device 30, shown separately in FIG. 3A, is a generally cylindrical member 32 having an arcuate trough 34 at one end preferably culminating in a sharp tip 36, which is used, for example, to puncture through the soft, or subcutaneous, tissues up to the scar-tissue-sheathed implanted devices, such as NORPLANT®. FIG. 3B illustrates an end-on view of the trochar device 30 shown in FIG. 3A. As illustrated in FIG. 1, the trochar device 30 slidably engages the tubular portion or cannula 22 and trough portions 24 of the sleeve device 20, and the tip 36 of the trochar device 30 preferably extends beyond the distal end of the trough portion 24 to pierce the soft or subcutaneous tissues. As shown in FIGS. 1, 2A and 3A, the handle portion 26 aligns the trochar device 30 in the trough portion 24 of the sleeve device 20, such that when the trochar device 30 is fully inserted into the sleeve device 20, a handle portion 38 of the trochar device 30 abuts a predesignated portion of the handle portion 26 of the sleeve device 20.

Figure 4A:
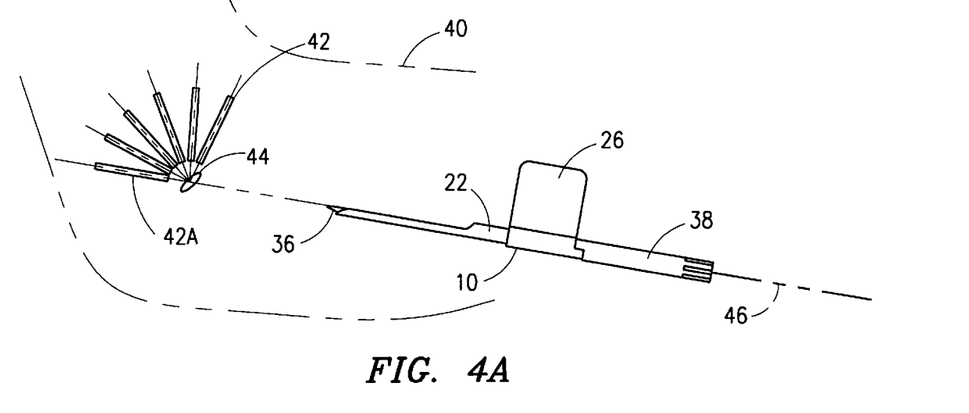
FIGS. 4A, 4B, 4C and 4D illustrate an operation employing the implant removal device of the present invention.

In operation, the improved method or technique set forth in the present invention is employed using the sleeve device 20, trochar device 30 and knife assembly 50 components shown in FIGS. 1–3 and 5. With reference now to FIG. 4A, there is generally illustrated an arm 40 having a number of implants 42 in the upper arm portion thereof, such as the aforedescribed NORPLANT® implants, arranged in a fan pattern from an original incision 44. In his arrangement, the implants are preferably disposed in a common plane and have a common point, typically the original incision opening, at which the respective axes of the implants intersect. In the preferred embodiment of the present invention, the original (approximately 4 mm) incision is reincised and used in the removal operation. As also shown in FIG. 4A, the portion of the removal device 10, including the combination of the sleeve device 20 and the trochar device 30, is oriented along an axis 46 of a particular implant 42A, and inserted subcutaneously toward the particular implant 42A, akin to sliding a needle toward a vein to start an intravenous injection.

Figure 4B:
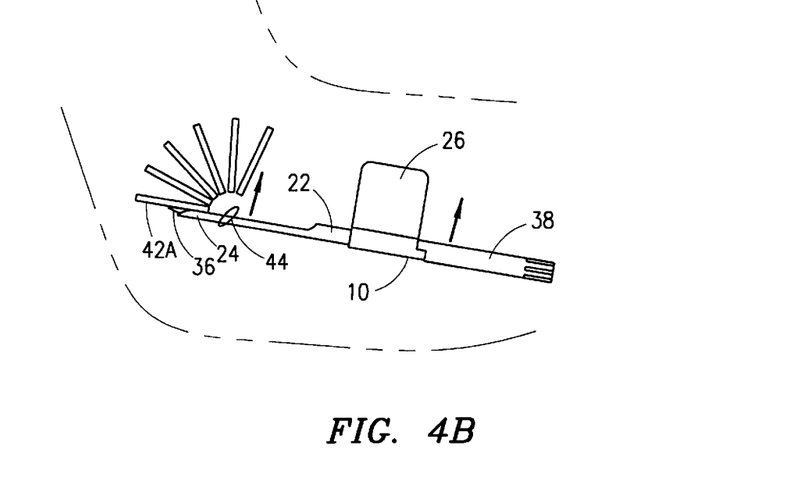

With reference now to FIG. 4B, the portion of removal device 10 is preferably advanced through the subcutaneous or soft tissues of the patient, using the sharp tip 36 of the trochar device 30, and under the particular implant 42A, again akin to sliding a needle under a vein. By now lifting the portion of the removal device 10 upwards towards the skin, as indicated by the arrows in FIG. 4B, the particular implant 42A is trapped between the portion of removal device 10 and the skin. Removal of the trochar device 30 from the sleeve device 20 leaves the sleeve device 20 disposed below the particular implant 42A. In particular, the hemicylindrical trough portion 24 of the sleeve 20 is disposed below the envelope of scar tissue surrounding the particular implant 42A, thereby trapping it between the trough portion 24 and the skin. Although the implant 42A may be readily discerned by palpitation at this point, the surrounding scar-tissue-sheath anchors the implant, thereby inhibiting removal of the implant, and must be incised. However, the scar tissue sheath of implant 42A is under the skin, so it cannot be visualized for incision.

Figure 5A:
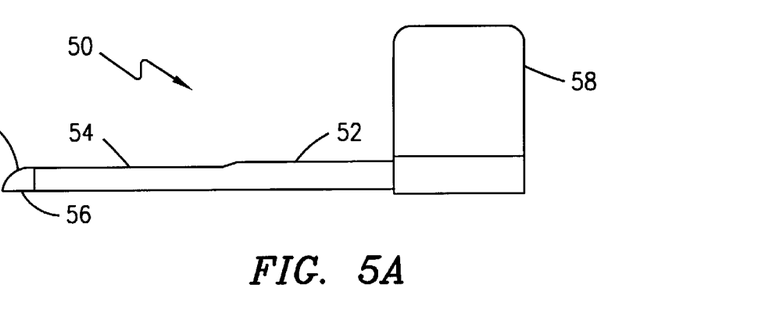
Figure 5B:
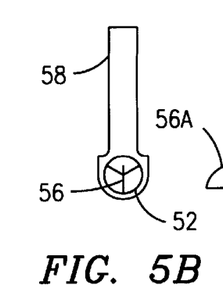

With the implant 42A positioned and trapped within the trough portion 24 of the sleeve device 20, an improvement of the present invention entails insertion of the knife assembly 50, illustrated in more detail in FIGS. 5A and 5B, into the tube portion 22 and trough portion 24 previously occupied by the trochar device 30. The knife assembly 50 has a generally cylindrical member 52 providing an elongated support section, which may also have an arcuate portion 54 therein, for a knife, e.g., a blade 56, affixed to and extending outwardly from a distal end of the cylindrical member 52. The blade 56 is preferably "guarded", i.e., it can not cut through the wall of the implant, since only a limited portion of the blade 56 is exposed when affixed to the support section. Also, the blade 56 is preferably contained within the contours of the sleeve device 20 as a further guard to prevent contact with and trauma to surrounding tissue. The knife assembly 50 also employs a handle portion 58 aligned with the blade 56, so that the rotational orientation of the blade 56, when disposed under the skin, is easily determined by the user by reference to the orientation of the handle portion 58. The handle portion 58 is desirably made of plastic or other such material, and is used to manipulate the orientation of the cutting blade 56, as described hereinabove.

Figure 4C:
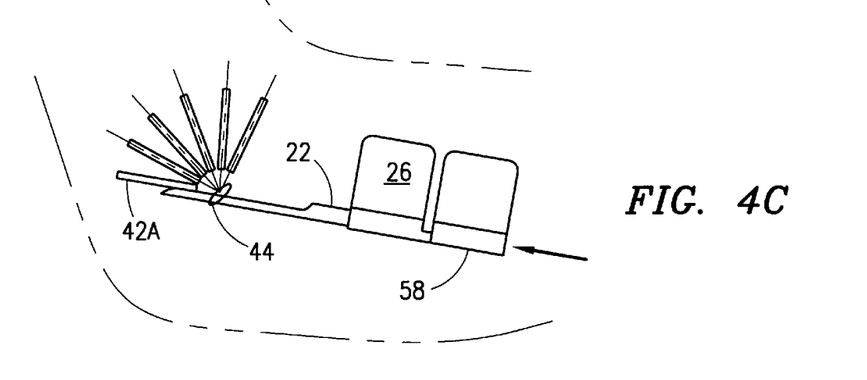

With reference now to FIG. 4C, after removal of the trochar device 30 and insertion of the knife assembly 50 into the cannula 22 of the sleeve device 20 and along the trough portion 24 thereof, the blade 56 is used to cut the end and/or length of the scar-tissue-sheath surrounding the particular implant 42A trapped therein without the need to visually observe the scar-tissue-sheath itself. As shown in FIGS. 5A and 5B, the blade 56 has a sharp tip or cutting edge portion 56A to cut the scar tissue when pushed therein. By rotating the orientation of the blade 56 within the sleeve device 20, i.e., by rotating the handle portion 58 and the cylindrical member 52, multiple cuts at a variety of angles may be employed to locally shred the scar envelope and free the encased implant 42A with minimal or no damage to any surrounding non-scar tissue.

Figure 4D:
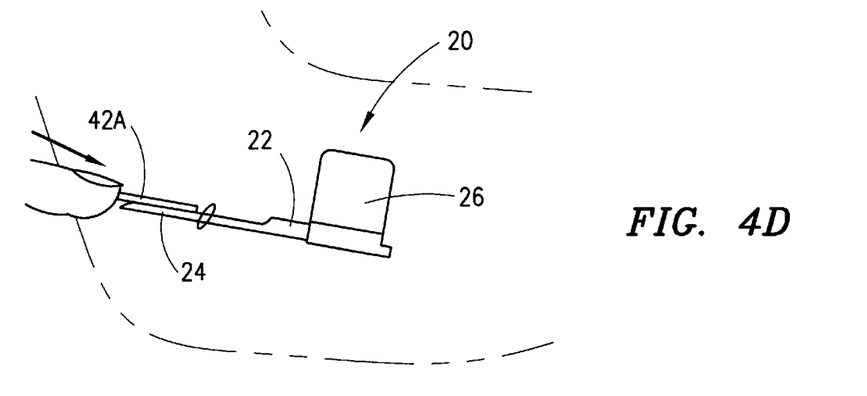
Figure 6:
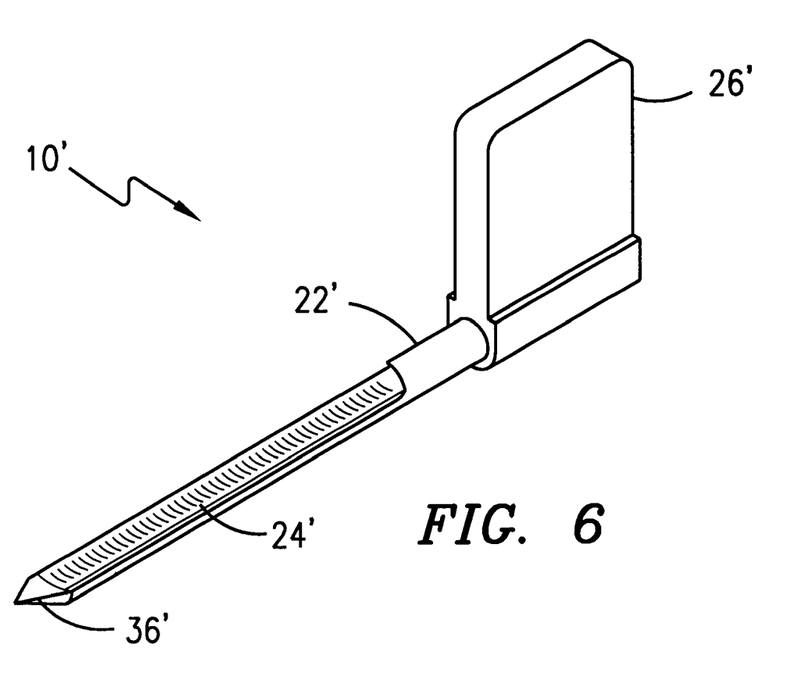
FIG. 6 is a perspective view of another embodiment of a portion of the implant removal device as set forth in the present invention, illustrating a sleeve device with a pointed tip.

In an alternative embodiment of the present invention, illustrated in FIG. 6 and generally designated by the reference numeral 10', the sleeve 20 and trochar devices 30 of FIGS. 2A, 2B, 3A and 3B are integrated into one component, i.e., a tube portion or cannula 22' having a pointed tip 36'. In this embodiment, common portions of the above-described surgical device of the first embodiment are represented by the same reference numbers, followed by a prime symbol ('). In this arrangement, the distal end of the elongated trough portion 24' of the tube portion 22' has a sharp point or tip 36' adapted to penetrate the subcutaneous soft flesh tissue. The trough portion 24' is thus adapted to penetrate soft tissue under the scar-tissue-sheath surrounding the implanted device. Further, in this embodiment, the removable knife assembly 50 of FIGS. 5A and 5B is insertable through the tube portion 22' and trough portion 24' of the sleeve device portion with the blade 56 disposed at the distal end of the removable knife assembly 50 extending substantially to the distal end of the trough portion 24'. Surgical removal of the particular implant 42A is carried out in the same manner as described above with respect to use of a surgical device having the removable trochar device 30, with the exception that when using this alternate embodiment of the surgical device, it is not necessary to remove a separate trochar device 30 prior to inserting the knife assembly 50. In either embodiment, by digitally manipulating the implant 42A through the incision in the scar-tissue-sheath, such as by using a finger as illustrated in FIG. 4D, the implant 42A is deposited or expressed onto the trough portion 24 or 24' and readily brought out the incision hole 44. By altering the alignment of the implant removal device and repeating the above, the remaining implants 42 may also be expressed, as is understood by one skilled in the art.

It should be understood that the particular size and placement of the implants, e.g., the current NORPLANT® fan-like distribution of six capsules, are illustrative and do not delimit the scope of the present invention. For example, the technology in the NORPLANT® SYSTEM is moving toward fewer implants, e.g., two, that administer the requisite dosage. Since the size of these new implants would most likely be larger than the current capsules, the size of the removal apparatus of the present invention would preferably be larger as well to handle the new product configuration. It should further be understood that although FIGS. 4A–4D illustrate a preferred, orderly, fan-like distribution of the implanted devices, the principles and teachings of the present invention are equally applicable to scenarios where the implanted devices are skewed, crimped, distorted or otherwise misaligned with respect to each other or bodily arrangements.

It should also be understood that the insertable components of the present invention, i.e., the tubular and cylindrical portions 22, 32 and 52 of the sleeve device 20, trochar device 30 and knife assembly 50, respectively, are preferably made of stainless steel or other biologically or surgically compatible materials. The remaining components, i.e., for the handles 26, 38 and 58 of the sleeve device 20, trochar device 30 and knife assembly 50, respectively, are preferably made of a resin or plastic material which provides a sufficient grip for manipulating the surgical portions. Furthermore, the components of the surgical implant device, i.e., the sleeve device 20, trochar 30 and the knife assembly 50, may individually be made through a one-piece injection molding process, as is well understood in the injection molding arts, provided the molded components are made of a surgically compatible material.

It should additionally be understood that the principles and teachings of the present invention may be practiced in the removal of a variety of implanted devices having a variety of dimensions. It should, therefore, be understood that the scope of the claims are not limited to the removal of NORPLANT® or other contraceptive capsules, but may cover other implanted devices for drug delivery or other purposes. Accordingly, the dimensions or diameters of the implant devices removable by virtue of the teachings of the present invention varies, e.g., about 1.0 to 5.0 mm, about 2.0 to 3.0 mm, about 2.3 mm to 2.5 mm and about 2.4 mm, the current diameter of the NORPLANT® capsules. Applicant understands that Wyeth Ayerst, the manufacturer of the NORPLANT SYSTEM has received FDA approval of another levonorgestrel implant device labeled NORPLANT II, which Applicant believes may utilize fewer and large capsules. At present, the FDA information on NORPLANT II capsules indicates an approximate diamater of 2.5 mm and a length of 43 mm. Applicants apparatus and method are nonetheless intended to cover the removal of these proposed NORPLANT II capsules and any other like implanted devices.

Although preferred embodiments of the system and method of the present invention have been illustrated in the accompanying drawings and described in the foregoing detailed description, it will be understood that, the invention is not limited to the embodiments disclosed, but is capable of numerous rearrangements, modifications and substitutions without departing from the spirit of the invention as set forth and defined by the following claims.

What is claimed is:

1. A surgical device for removing implanted devices, said surgical device comprising:

a sleeve device having a handle portion, a tubular portion thereof being aligned in a predetermined relationship with said handle portion, and a trough portion extending outwardly from said tubular portion and in alignment therewith, said trough portion having a tip disposed at a distal en& thereof; and a removable knife assembly adapted to be selectively insertable through said tubular portion of said sleeve device, said knife assembly having an elongated support section, a handle attached to said support section, and a blade disposed at a distal end of said support section, said support section having a length sufficient to position said blade substantially at the tip of said trough portion of the sleeve device for selectively cutting subcutaneous flesh tissue when the removable knife assembly is inserted through said tubular portion of the sleeve device, said selective cutting of said subcutaneous flesh tissue by said blade being along a cutting axis substantially parallel to the axis of movement of said removable knife assembly within said sleeve device and selectively oriented thereabout.

2. The surgical device, as set forth in claim 1, wherein said tip disposed at the distal end of said trough portion has a sharp point adapted to penetrate subcutaneous flesh tissue.

3. The surgical device, as set forth in claim 1, wherein said surgical device further comprises a removable trochar device having a handle portion adapted to abut a predesignated portion of the handle portion of the sleeve device, and a generally cylindrical member extending outwardly from said handle portion of the trochar device and adapted to be slidably received in the tubular and trough portions of said sleeve device, and having a length sufficient to extend a distal end thereof beyond the tip of the elongated trough portion of the sleeve device when the removable trochar device is inserter through said sleeve portion of the sleeve device, said trochar device having a sharp tip at the distal end thereof adapted to puncture subcutaneous flesh tissue when the sharp tip is extended beyond the distal end of the trough portion of the sleeve device.

4. The surgical device, as set forth in claim 3, wherein said trochar device has an arcuate trough portion disposed adjacent the distal end of the cylindrical member.

5. The surgical device, as set forth in claim 3, wherein said trochar device is made of a biologically compatible material.

6. The surgical device, as set forth in claim 1, wherein said blade disposed at the distal end of the support section of the removable knife assembly has a distal cutting edge and a guard means spaced a predetermined distance from the distal cutting edge whereby the penetration of the blade into flesh tissue or said implanted devices is limited to the predetermined distance said guard means is spaced from the distal cutting edge of the blade.

7. The surgical device, as set forth in claim 1, wherein said surgical device is made of a biologically compatible material.

8. The surgical device, as set forth in claim 7, wherein tubular and trough portions of said sleeve device, and said support section and blade of said knife assembly are made of stainless steel.

9. The surgical device, as set forth in claim 7, wherein said handle portions of said sleeve device and said knife assembly are made of a material selected from the group consisting of resin and plastic.

10. The surgical device, as set forth in claim 7, wherein at least one of said sleeve device and said knife assembly are made of a one-piece injection molded material.

11. A surgical device adapted for the removal of contraception capsules, the combination of surgical device and contraception capsules comprising:
a sleeve device having a handle portion, a tubular portion thereof being aligned in a predetermined relationship with said handle portion, and a trough portion extending outwardly from said tubular portion and in alignment therewith, said trough portion having a tip disposed at a distal end thereof; and
a removable knife assembly adapted to be selectively insertable through said tubular portion of said sleeve device, said knife assembly having an elongated support section, a handle attached to said support section, and a blade disposed at a distal end of said support section, said support section having a length sufficient to position said blade substantially at the tip of said trough portion of the sleeve device for selectively cutting subcutaneous flesh tissue when the removable knife assembly is inserted through said tubular portion of the sleeve device, said selective cutting of said subcutaneous flesh tissue by said blade being along a cutting axis substantially parallel to the axis of movement of said removable knife assembly within said sleeve device and selectively oriented thereabout.

12. The surgical device, as set forth in claim 11, wherein in said combination said contraceptive capsules contain levonorgestrel.

13. The surgical device, as set forth in claim 11, wherein in said combination said contraceptive capsules comprise NORPLANT SYSTEM® or NORPLANT II capsules, said trough portion of said sleeve device being adapted to receive said NORPLANT SYSTEM® or NORPLANT II capsules therein.

14. The surgical device, as set forth in claim 1, wherein said trough portion of said sleeve device is configured to receive contraceptive capsules having a diameter of about 1.0 to 5.0 mm.

15. The surgical device, as set forth in claim 14, wherein said trough portion of said sleeve device is configured to receive contraceptive capsules having a diameter of about 2.0 to 3.0 mm.

16. The surgical device, as set forth in claim 15, wherein said trough portion of said sleeve device is configured to receive contraceptive capsules having a diameter of about 2.3 to 2.6 mm.

17. The surgical device, as set forth in claim 16, wherein said trough portion of said sleeve device is configured to receive contraceptive capsules having a diameter of about 2.4 mm.

18. The surgical device, as set forth in claim 16, wherein said trough portion of said sleeve device is configured to receive contraceptive capsules having a diameter of about 2.5 mm.

19. A method for surgically removing an implanted device from a patient, comprising:
palpating the surface of the patient's skin in an area above the proximate position of the implanted device and determining the position and orientation of said implanted device;
defining an axis aligned with said implanted device;
incising an opening through the skin at a position proximate an end of said implanted device;
aligning a surgical device having a sleeve device with an elongated trough portion with said opening in the skin and said implanted device;
inserting said surgical device through said opening and advancing a distal end of the elongated trough portion of the sleeve device so that at least a portion of the trough portion is positioned below said implanted device;
lifting said trough portion of the sleeve device toward the skin, thereby trapping said implanted device between the trough portion and the skin;
inserting a removable knife assembly of said surgical device through a tubular portion of said sleeve device;
advancing said removable knife assembly through said tubular portion until a blade disposed on a distal end of said knife assembly is positioned substantially at a distal end of the elongated trough portion of the sleeve device;
reciprocating said knife assembly within said tubular portion of the sleeve device, whereby flesh surrounding said end of the implanted device is opened sufficiently to permit said implanted device to pass therethrough;
withdrawing said removable knife assembly from said sleeve device;
applying fingertip pressure to the skin surface above said implanted device and manually urging said implanted device into the trough portion of the sleeve device and through said incised opening; and
removing said implanted device from the trough portion of the sleeve device.

20. The method for surgically removing an implanted device, as set forth in claim 19, wherein said surgical device includes a removable trochar device adapted to be slidably received in the tubular and rough portions of the sleeve device, and wherein prior to said step of inserting said surgical device through said opening, said method further comprises the step of sliding said trochar device through said tubular and trough portions of the sleeve device, combining said sleeve and trochar devices, said step of inserting comprising inserting the combined sleeve and trochar devices through said opening.

21. The method for surgically, removing an implanted device, as set forth in claim 20, wherein said method further comprises the step of:

withdrawing the removable trochar device from the tubular and trough portions of the sleeve device prior to inserting the removable knife assembly through the tubular portion of the sleeve device.

22. The method for surgically removing an implanted device, as set forth in claim 19, wherein said incising an opening through the skin at a position proximate the end of said implanted device comprises incising said opening at a position previously incised for the insertion of said implanted device.

23. The method for surgically removing an implanted device, as set forth in claim 19, wherein said method further comprises the step of:

sequentially surgically removing a plurality of implanted devices from respective proximal ends of the implanted devices through a common opening.

* * * * *

UNITED STATES PATENT AND TRADEMARK OFFICE
CERTIFICATE OF CORRECTION

PATENT NO. : 6,053,927
DATED : April 25, 2000
INVENTOR(S) : Robert S. Hamas

Page 1 of 1

It is certified that error appears in the above-identified patent and that said Letters Patent is hereby corrected as shown below:

Column 2,
Line 48, replace "cain" with -- can --

Column 4,
Line 60, replace "tho" with -- the --

Column 5,
Line 45, replace "(detail" with -- detail --

Column 6,
Line 10, replace "his" with -- this --

Column 8,
Line 49, replace "en&" with -- end --

Column 9,
Line 11, replace "inserter" with -- inserted --

Column 11,
Line 4, replace "rough" with -- trough --

Signed and Sealed this

Thirtieth Day of October, 2001

Attest:

*Nicholas P. Godici*

NICHOLAS P. GODICI
*Attesting Officer*     *Acting Director of the United States Patent and Trademark Office*